United States Patent [19]

Klingenstein

[11] Patent Number: 5,730,726
[45] Date of Patent: Mar. 24, 1998

[54] APPARATUS AND METHOD FOR REMOVING FECAL IMPACTION

[76] Inventor: Ralph James Klingenstein, 151 Tremont St., Apt. 23E, Boston, Mass. 02111

[21] Appl. No.: 610,213

[22] Filed: Mar. 4, 1996

[51] Int. Cl.⁶ .................................................. A61M 29/00
[52] U.S. Cl. .......................... 604/105; 604/104; 604/73; 604/54; 606/127
[58] Field of Search ............................... 604/104, 54, 73, 604/105, 106; 606/127, 197, 198

[56] References Cited

U.S. PATENT DOCUMENTS

| | | |
|---|---|---|
| 833,759 | 10/1906 | Sourwine . |
| 1,448,158 | 3/1923 | Sims . |
| 1,828,986 | 10/1931 | Stevens . |
| 1,972,428 | 9/1934 | Richard . |
| 3,316,912 | 5/1967 | Whitaker . |
| 3,495,586 | 2/1970 | Regenbogen ............... 604/105 |
| 4,243,037 | 1/1981 | Smith ........................ 128/303 R |
| 4,471,782 | 9/1984 | Shuffield .................... 128/341 |
| 5,000,750 | 3/1991 | Leveen et al. ............. 606/1 |
| 5,190,555 | 3/1993 | Wetter et al. .............. 606/114 |
| 5,199,419 | 4/1993 | Remiszewski et al. ... 128/20 |
| 5,381,788 | 1/1995 | Matula et al. .............. 128/20 |

FOREIGN PATENT DOCUMENTS

| | | |
|---|---|---|
| 2 380 018 | 9/1978 | France . |
| 3340581 C1 | 6/1985 | Germany . |
| 1169419 | 11/1969 | United Kingdom . |
| WO 91/03983 | 4/1991 | WIPO . |
| WO 93/02732 | 2/1993 | WIPO . |

OTHER PUBLICATIONS

Keith Wrenn, M.D., "Fecal Impaction," *The New England J. of Medicine*, pp. 658–662 (Sep. 7, 1989).
Kokoszka et al., "Treatment of Fecal Impaction with Pulsed Irrigation Enhanced Evacuation," Department of Surgery, *University of Illinois College of Medicine at Chicago*, 37(2):161–164 (1994).

*Primary Examiner*—Michael Powell Buiz
*Assistant Examiner*—N. Kent Gring
*Attorney, Agent, or Firm*—Testa, Hurwitz & Thibeault, LLP

[57] ABSTRACT

An apparatus for removing a fecal impaction from a patient's rectum is disclosed. The apparatus comprises a shaft which is inserted into the patient's rectum. Coupled to the shaft is a plurality of flexible spines. The apparatus also includes a mechanism for bowing at least one of the spines away from the shaft in order to cut through the fecal mass and define a volume that includes at least a portion of the fecal impaction to be removed. In one aspect, the mechanism for bowing at least one of the spines away from the shaft is a fixed collar which defines a plurality of flexible spine orifices. Each of the flexible spines passes a predetermined length through one of the spine orifices. In another aspect, the mechanism for bowing the spines is a collar slideably mounted to the shaft. In this aspect, each one of the plurality of flexible spines is coupled to the slideable collar. In another aspect, the apparatus includes a sheath having an edge fixed to the closer end of the flexible spines and a movable edge which can be extended to cover the flexible spines and encapsulate the fecal mass. Once the fecal mass is encapsulated by extending the sheath over the bowed spines, the fecal mass can be flattened by straightening the spines and subsequently removed.

32 Claims, 3 Drawing Sheets

APPARATUS AND METHOD FOR REMOVING FECAL IMPACTION

FIELD OF THE INVENTION

The present invention relates to a medical apparatus and method and, in particular, to a medical apparatus and method for removing a fecal impaction from the rectum of a patient.

BACKGROUND OF THE INVENTION

Fecal impaction is a term for a rectal fecal mass which generally will not move distally without physician intervention. While fecal impaction can occur in any age group, it is especially common in certain groups, such as incapacitated or institutionalized elderly people.

The causes of fecal impaction vary. Use of narcotics predisposes a patient to fecal impaction. Also, agents used to treat depression and psychosis, such as tricyclic antidepressants and phenothiazines, can cause fecal impaction due to their anticholinergic properties. Other medication can also predispose patients to fecal impaction. The long term use of stimulant laxatives damages the myenteric plexus, and even the use of bulk forming laxatives such as psyllium seed with insufficient hydration may cause fecal impaction.

The elderly population is especially predisposed to fecal impaction for a number of reasons. Lack of mobility plays a part; upright posture and exercise have been shown to promote colonic motility. Among elderly people with dementia, neglecting the urge to defecate contributes to constipation and can lead to fecal impaction. Dehydration can also compound the problem. Similarly, a decreased intake of fiber and a lack of variety in meals have also been implicated. Elderly people have more situational depression and take more antidepressant medications than younger people. All of these factors contribute to increase their predisposition to fecal impaction.

Whatever the cause of fecal impaction, enduring a fecal impaction and its treatment may cause severe humiliation and obstruction of the large bowel is common with fecal impaction. Mortality among patients with obstruction and impaction ranges from 0–16%, depending on the population; it is higher among the very young and the very old.

The traditional treatments for fecal impaction are enema installation, spinal anesthesia with surgical disimpaction, or digital manipulation. Although enemas and suppositories alone may eliminate the impaction, the manual fragmentation and extraction of the fecal mass are almost required, as efforts to remove the entire fecal mass by catharsis from above, may be ineffectual and may worsen the abdominal pain or contribute to complications.

Surgical disimpaction operations such as total colectomy with ileosigmoid or ileorectal anastomosis have met with varied success. High rates of complications and mortality can be expected in elderly patients.

Digital manipulation is accomplished by a doctor or registered nurse physically inserting their fingers into the rectum of the patient and using a scissoring action to breakup the hardened stool. This procedure is difficult, time consuming, uncomfortable, and annoying to both the patient and the care-giver, can result in a tearing of the rectum wall by the fingernail of the doctor or registered nurse, and does not work well.

It is therefore desirable to provide an apparatus for removing a fecal impaction from a patient's rectum that avoids the need for surgical intervention as well as the discomfort and dangers associated with digital manipulation of the hardened stool. The present invention provides the aforementioned desirable characteristics while avoiding the undesirable characteristics of the prior art.

SUMMARY OF THE INVENTION

The present invention relates to an apparatus and method for removing a fecal impaction from a patient's rectum. In one aspect, the apparatus includes a shaft having proximal and distal ends. The distal end of the shaft may be substantially conical to facilitate introduction of the shaft into the patient's rectum.

Attached to the proximal end of the shaft are a plurality of flexible spines that are arranged parallel to the shaft. The spines may be fixed directly to the shaft, or they may be coupled to a collar which is fixed to the proximal end of the shaft.

At least one of the spines can be bowed away from the shaft. The bowed spine cuts through the fecal impaction and defines a volume between itself and the shaft which contains some portion of the fecal impaction.

In one embodiment, the flexible spines are coupled to a collar that is slideably mounted to the distal end of the shaft. Sliding the collar causes the flexible spines to bow. In another embodiment, the distal ends of the spines are coupled to the distal end of the shaft and the shaft is collapsible along a longitudinal axis. In this embodiment, collapsing the shaft causes the flexible spines to bow outwardly.

In yet another embodiment, the flexible spines are bowed by a plurality of rods which can be extended radially from the shaft. In some embodiments the rods are located at the distal end of the shaft and push the distal ends of the flexible spines away from the shaft. In other embodiments the rods are located near the middle of the shaft and push outwardly on the middle of the flexible spines.

In another aspect, a collar is fixed to the proximal end of the shaft and the collar has a number of orifices. A plurality of flexible spines are attached to the distal end of the shaft and extend some length through the orifices defined by the collar. The spines may be fixed directly to the distal end of the shaft, or they may be coupled to a collar fixed at the distal end of the shaft. The spines may be bowed by a plurality of rods that can be extended radially from the shaft.

In some embodiments the apparatus also includes a sheath. The sheath is fixed at the proximal end of one or more of the spines and has a movable edge which is slideably coupled to at least one of the spines. The sheath can be extended to cover the spines from end to end which encapsulates the volume defined by the shaft and the bowed spines. In some embodiments the sheath is extended with a wire that is coupled to the movable edge of the sheath. In other embodiments the sheath includes a plurality of rings which are slideably attached to the spines.

In another aspect of the invention, a method for removing a fecal impaction from a patient's rectum begins by inserting an apparatus as described above into the patient's rectum. The apparatus may be inserted through the fecal impaction or it may be inserted to one side of the impaction.

At least one of the flexible spines is bowed away from the shaft. In some embodiments all of the flexible spines are bowed away from the shaft. The bowed spines cut through the fecal impaction. The sheath is extended along the length of the bowed spines in order to encapsulate some portion of the fecal impaction. The bowed spines are straightened to compress the fecal impaction and the apparatus is removed from the patient's rectum. In some embodiments a lubricant is disposed on the outside surface of the sheath in order to facilitate the removal step.

In other embodiments the method is begun by inserting an apparatus which has a shaft, a collar slideably mounted on the distal end of the shaft, and a number of flexible spines which are attached proximally to the shaft and distally to the collar. In these embodiments, the flexible spines are bowed by sliding the collar toward the proximal end of the shaft.

In another aspect of the invention, an apparatus includes a shaft having a proximal end, a distal end, and a longitudinal axis. A flexible spine is coupled both proximally and distally to the shaft and is fixed in position. A second flexible spine is also coupled proximally and distally to the shaft but is rotatable about the longitudinal axis of the shaft. A sheath is coupled to both spines, and the spines may be bowed away from the shaft.

This apparatus is used by inserting it through the fecal impaction that is to be removed. Both spines are bowed away from the shaft and the rotatable spine is rotated around the shaft. When rotated around the shaft, the spine cuts through the fecal impaction and deploys the sheath to encapsulate the fecal impaction. The spines are straightened. This flattens the fecal mass and the apparatus is removed from the patient's rectum.

In another aspect of the invention, an apparatus for removing a fecal impaction from a patient's rectum includes a shaft having proximal and distal ends which defines a wire channel running along its length. The distal end of the shaft defines a wire orifice, and the proximal end of the shaft defines a handle orifice.

The apparatus also includes a collar slideably mounted on the distal end of the shaft. A number of flexible spines are attached distally to the slideable collar and proximally to the shaft.

The apparatus also includes a sheath, which can be folded accordion-like at the proximal end of the shaft, fixed to the proximal ends of the spines and having a slideable edge mounted to at least one of the flexible spines. The slideable edge is stiff enough to cut through the fecal impaction. A wire is coupled to the sheath, extends through the wire orifice, runs through the wire channel, and exits the handle orifice to provide the user of the apparatus with a way of extending the sheath over the bowed spines. In some other embodiments, the moveable edge of the sheath is pushed by rods. In still other embodiments, the moveable edge of the sheath is both pushed by rods and pulled by a wire.

BRIEF DESCRIPTION OF THE DRAWINGS

The invention is pointed out with particularity in the appended claims. The above and further advantages of this invention may be better understood by reference to the following description taken in conjunction with the accompanying drawings, in which:

DETAILED DESCRIPTION OF THE INVENTION

Referring now to FIGS. 1A–1B and 2A–2B, an apparatus for removing a fecal impaction, shown generally as 10, has a shaft 12, a plurality of flexible spines 14 arranged parallel to the shaft 12, and structure for bowing the flexible spines 14.

Figure 1A:
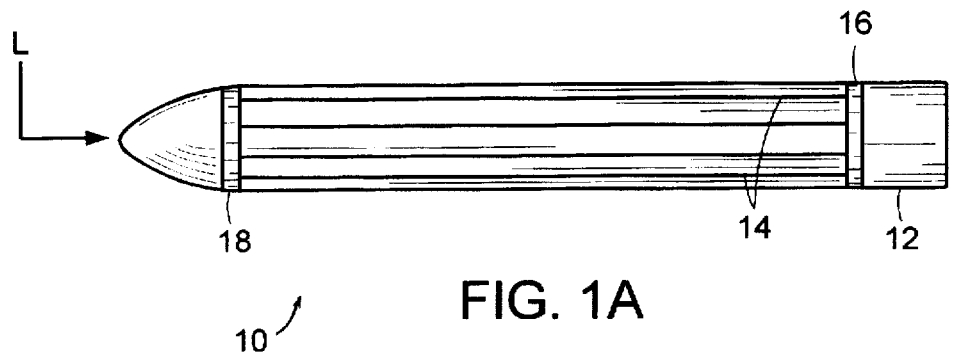
FIG. 1A is a side view of an embodiment of the apparatus for removing a fecal impaction showing a slideable collar coupled to the distal end of the shaft and the flexible spines in an unbowed configuration coupled to a collar fixed to the proximal end of the shaft.
Figure 1B:
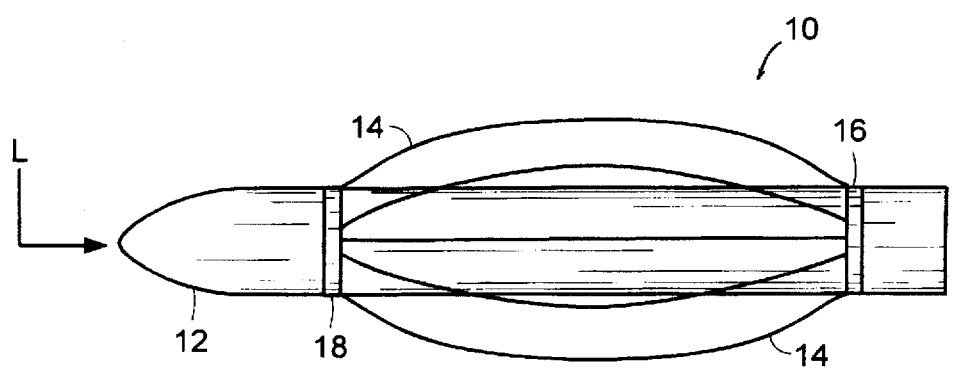
FIG. 1B is a side view of the embodiment shown in FIG. 1A showing the spines in a bowed configuration.

FIGS. 1A and 1B show an embodiment of the apparatus in which the proximal end of the flexible spines 14 are coupled to a collar 16, which is itself fixed to the proximal end of the shaft 12. In alternative embodiments, the spines 14 may be coupled directly to the proximal end of the shaft 12 and may even be of unitary construction with the shaft 12.

For the embodiment shown in FIGS. 1A and 1B, the structure for bowing the flexible spines 14 can be a collar 18 slideably mounted on the distal end of the shaft 12. In one embodiment, the collar may be annular, having an inner diameter slightly larger than the outer diameter of the shaft 12 in order to permit displacement of the collar 18 along the longitudinal axis, L, of the shaft 12.

The distal ends of the flexible spines 14 are coupled to the slideable collar 18. Displacement of the slideable collar 18 proximally along the longitudinal axis of the shaft 12 causes the flexible spines 14 to bow outwardly (shown in FIG. 1B). In one embodiment the slideable collar 18 can be pulled toward the proximal end of the shaft 12 by a rod connected to the slideable collar 18. The rod may be disposed inside the shaft 12 and protrudes from the proximal end of the shaft 12. Pulling the rod causes the slideable collar 18 to be pulled toward the proximal end of the shaft 12 and the resultant pressure on the spines 14 causes them to bow away from the shaft 12.

Figure 5:
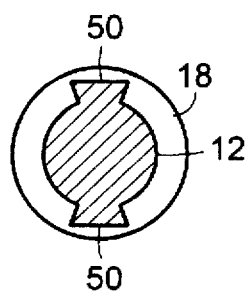
FIG. 5 is a highly diagrammatic cross-sectional view of a shaft showing collar bosses.

The pressure on the flexible spines 14 may cause the slideable collar 18 to begin rotating due to the pressure exerted on it by the bowed spines 14. It may be desirable to provide the shaft 12 with one or more collar bosses 50 (shown in FIG. 5) in order to prevent the slideable collar 18 from rotating when it is displaced proximally. The collar bosses would interlock with channels or grooves in the slideable collar 18, thereby preventing the collar from rotating when pulled proximally to bow the spines 14.

Figure 6:
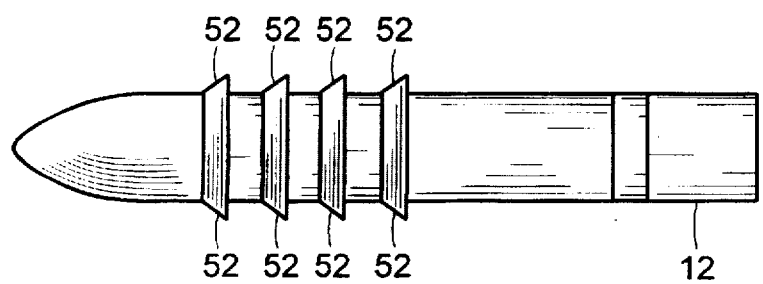
FIG. 6 is a highly diagrammatic side view of a shaft showing locking detents.

In other embodiments, the slideable collar 18 may be provided with a locking mechanism to prevent it from sliding back once displaced along the longitudinal axis. For example, the shaft 12 may be provided with a number of locking detents 52 (shown in FIG. 6) which allow the slideable collar 18 to be displaced proximally but prevent it from sliding back distally until the detents are released.

Figure 2A:
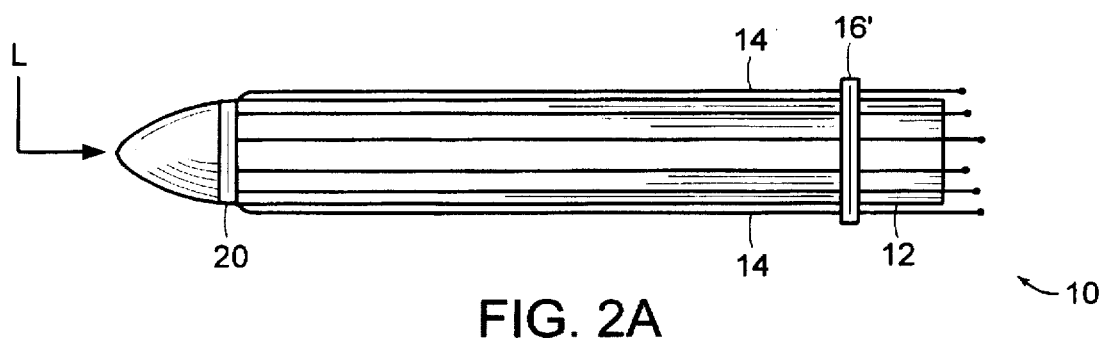
FIG. 2A is a side view of an embodiment of the apparatus for removing a fecal impaction showing a fixed collar coupled to the proximal end of the shaft which defines spine orifices and the flexible spines in an unbowed configuration coupled to a collar fixed to the distal end of the shaft.
Figure 2B:
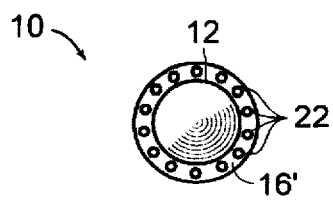
FIG. 2B is a back view of the embodiment shown in FIG. 2A.

In the embodiment shown in FIGS. 2A and 2B, the flexible spines 14 are coupled to the distal end of the shaft 12. In one embodiment, the spines 14 are coupled distally to a collar 20 which is itself fixed to the distal end of the shaft 12. Alternatively, the flexible spines 14 may be coupled directly to the distal end of the shaft 12 or the spines 14 may be of unitary construction with the shaft 12.

In FIGS. 2A–2B, the means for bowing the flexible spines 14 is a fixed collar 16' which defines a plurality of flexible spine orifices 22. Each of the flexible spines 14 extends a predetermined length through one of the flexible spine orifices 22. The flexible spine orifices 22 should be large enough so that spines 14 may be pushed through the orifices 22. The flexible spine orifices 22 should be small enough so that the flexible spines 14 bow when pushed through the orifices 22. In one embodiment, the flexible spine orifices 22 may be fitted with a mechanism for securing the spines 14 in a bowed position once they have been pushed through an orifice 22; for example, each spine orifice 22 may be fitted with a clamp to hold the individual spines 14.

In other embodiments, the structure for bowing the flexible spines 14 can be a number of rods which can be extended radially from the shaft 12. The rods may be located near the distal ends of the shaft 12. In this embodiment, the proximal ends of the spines 14 are coupled to the proximal end of the shaft 12, and the distal ends of the spines 14 are connected to the rods. When the rods are extended, the spines 14 are pushed away from the shaft.

In an alternative embodiment, the rods are located near the center of the shaft 12, and bow the spines 14 outwardly by exerting pressure on the center of the flexible spines 14. In this embodiment, the spines 14 may be coupled proximally to the shaft 12 and distally to a slideable collar 18. Alternatively, the spines 14 may be coupled distally to the shaft 12, with their proximal ends extending a predetermined length through a number of spine orifices 22.

The shaft 12 may be substantially cylindrical in shape. In general, the shaft 12 can be any shape that fits comfortably inside the rectum of a patient. Whatever shape is selected, the shaft 12 should be from 5 cm to 15 cm in length, and have a diameter from 0.5 cm to 3.0 cm. As shown in FIG. 1, the distal end of the shaft 12 can have a substantially conical shape. The shape of the distal end of the shaft 12 should be selected to facilitate the insertion of the apparatus into the patient's rectum.

In one embodiment, the shaft 12 itself may be the structure for bowing the spines 14. In this embodiment, the flexible spines 14 are coupled to the proximal and distal ends of the shaft 12, and the shaft 12 is collapsible along its longitudinal axis. The resultant shortening of the shaft 12 causes the spines 14 to bow outwardly. As with other embodiments, the spines 14 may be coupled to collars that are fixed at the proximal and distal ends of the shaft 12.

In this embodiment, the shaft 12 may be telescoped along its longitudinal axis. Effectuating the shortening of the shaft 12 in this embodiment may be done by a screw mechanism, which allows the shaft to be telescoped while at the same time providing a shaft 12 that does not compress when first inserted into the rectum of a patient.

The shaft 12 may be manufactured from any material provided that the shaft 12 has sufficient structural integrity to be inserted into the rectum of a patient. The shaft 12 may be manufactured from various thermoplastics or metal. In general, the stronger the material from which the shaft 12 is manufactured, the smaller the diameter of the shaft 12 can become.

The flexible spines 14 may be manufactured of rigid plastic, surgical steel, or any other material that allows the flexible spines 14 to be made thin enough to cut through the fecal impaction. In general, a thinner spine 14 will cut through a fecal impaction more easily. In addition, the material selected should provide the spines 14 with the ability to bow 2.5 cm to 20 cm away from the shaft 12.

Figure 3A:
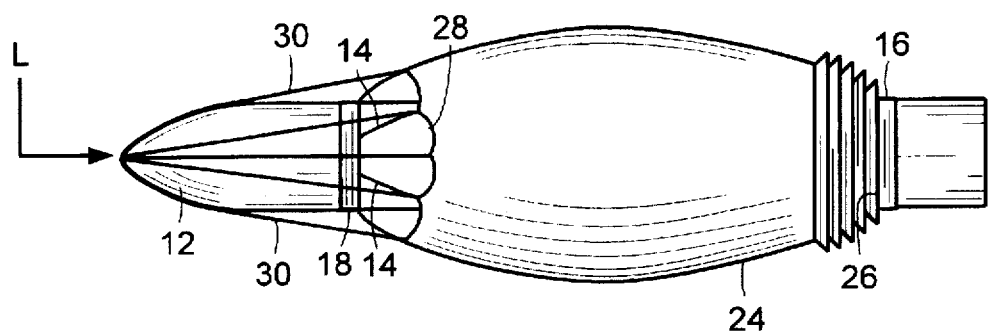
FIG. 3A is a side view of the apparatus of FIG. 1A showing a sheath partially disposed over the spines.
Figure 3B:
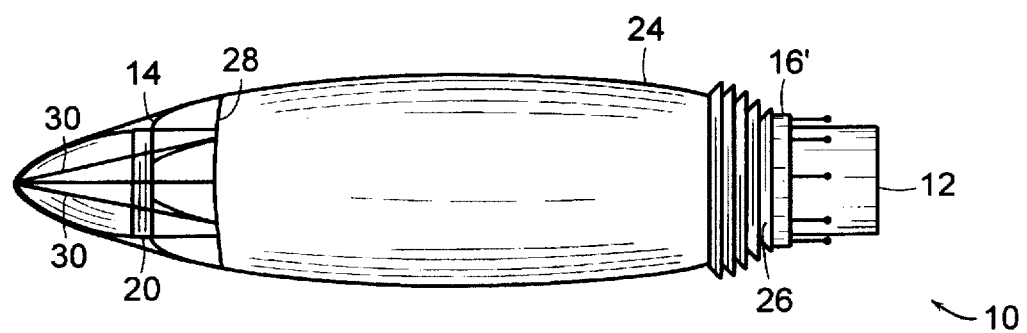
FIG. 3B is a side view of the apparatus of FIG. 2A showing a sheath partially disposed over the spines.

FIGS. 3A and 3B show embodiments of the apparatus that further include a sheath 24 disposed over the spines 14. When not extended, the sheath 24 may be folded up near the proximal end of the spines 14. The sheath 24 has a fixed end 26 and a slideable end 28.

The fixed end 26 of the sheath 24 may be coupled to the collar 16 or 16' which is fixed to the proximal end of the shaft. For example, the sheath 24 may be clamped between two separate pieces of the collar 16 or 16'. Alternatively the collar 16 or 16' may be provided with protuberances which hold the sheath 24. In another embodiment, the fixed end 26 of the sheath 24 may be coupled directly to the proximal ends of the flexible spines 14.

The moveable edge 28 of the sheath 24 can be displaced toward the distal end of the spines 14, in order to encapsulate the volume defined by the shaft 12 and the bowed, flexible spines 14. In one embodiment, the moveable edge 28 of the sheath 24 can be provided with a stiff, elastic band. The elastic band allows the moveable edge 28 of the sheath 24 to conform to the bowed spines 14 while, at the same time, the moveable edge 28 remains stiff enough to cut through the fecal impaction and facilitate its encapsulation.

In one embodiment, the moveable edge 28 of the sheath 24 is displaced by a wire 30 which is coupled to the moveable edge 28 at one or more points. Preferably, the wire 30 is coupled to the moveable edge 28 of the sheath 24 at multiple points to facilitate even displacement of the moveable edge 28. In another embodiment, a rod is attached to the moveable edge 28 of the sheath 24 at one or more points. The rod may be disposed in the shaft 12, and may be used to push and pull the moveable edge 28 of the sheath 24.

The sheath 24 can be slideably attached at various points along its length to at least one of the spines 14 to secure the sheath to the spines 14. The sheath 24 may be slideably attached to the flexible spines 14 by loops of surgical thread, by sleeves of the material which enclose the spines 14, or by a plurality of rings that are attached to the sheath 24 at various point along its length which slide along the flexible spines 14. The sheath 24 may be manufactured from any material that is stiff enough to compress adequately the encapsulated fecal impaction when the spines 14 are straightened. The sheath 28 can be manufactured from plastic or fabric.

Figure 4:
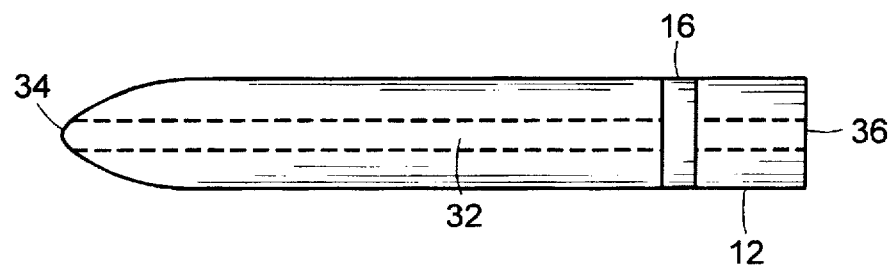
FIG. 4 is a highly diagrammatic side view of one embodiment of the shaft.

FIG. 4 depicts a shaft 12 for the present invention which defines a wire channel 32 (shown in phantom view) running the length of the shaft 12. The wire channel 32 should be large enough to accommodate the wire 30, while remaining small enough that it does not affect the structural integrity of the shaft 12. The wire channel 30 may be lubricated so that the wire can be pulled through it easily.

The wire channel 30 exits the shaft 12 at both ends, forming a wire orifice 34 and a handle orifice 36. The wire orifice 34 allows the wire 30 to exit the wire channel 32 and attach to the moveable edge 28 of the sheath 24. In one embodiment, the wire 30 protrudes from the handle orifice 36, runs through the wire channel 32, exits the shaft at the wire orifice 34. The wire 30 may then branch into multiple strands that are coupled to the moveable edge 28 of the sheath 24 at various points, or it may exit the wire orifice 34 and directly couple to the moveable edge 28 of the sheath 24.

In order to extend the sheath 24, the wire 30 is pulled where it protrudes from the handle orifice 36. If the wire 30 is manufactured from fabric, the edges of wire orifice 34 should be smooth so that the wire 30 does not break when pulled through the wire orifice 32. The shaft 12 may be provided with a mechanism to retain tension on the wire 30. For example, a boss may be provided at the proximal end of the shaft 12 and the wire 30 may be looped around the boss to hold the wire 30 in place.

When a user inserts the apparatus of FIGS. 1A–1B into the patient's rectum, the shaft 12 should be inserted through the fecal impaction. It is not necessary that the shaft 12 penetrate the exact center of the impaction. The shaft 12 should be inserted fully into the patient's rectum, that is, the shaft 12 should be inserted so that the point at which the spines 14 are coupled proximally to the shaft 12 is just inside the anus of the patient.

After insertion into the patient's rectum, the flexible spines 14 are bowed away from the shaft 12 to cut through the fetal impaction and define a volume inside the rectum which includes at least portion of the fecal impaction. This may be done by displacing a slideable collar 18 along the longitudinal axis of the shaft, or the shaft 12 may be collapsed in order to bow the spines 14. The spines 14 should be bowed far enough away from the shaft 12 to cut through and encompass at least a portion of the fecal impaction without harming the rectum of the patient.

After the flexible spines 14 are bowed to cut through the fecal impaction, the sheath 24 is extended to cover the flexible spines 14 from end to end. The sheath may be extended by pulling on a wire 30 connected to moveable edge 28 of the sheath 24. The sheath 24, when fully extended, encapsulates the volume defined by the bowed spines 14, which includes the fecal impaction.

Once the sheath 24 is fully extended, the spines 14 are straightened substantially to their original position. The sheath 24 compresses the encapsulated fecal impaction and the apparatus 10, along with the encapsulated fecal impaction, is removed from the patient's rectum. A lubricant may be disposed on the outside of sheath 24 to make this step easier.

Use of the embodiment of the apparatus shown in FIGS. 2A–2B is similar to the steps described above, except that, the shaft 12 may be inserted to one side of the fecal impaction as well as through the fecal impaction. If the shaft 12 is inserted to one side of the impaction, as few as one of the spines 14 may be bowed away from the shaft 12, because it is desirable to bow only the spines 14 that are adjacent to the impaction, and leave unbowed the spines 14 adjacent the rectum wall.

For instances in which the apparatus is inserted through the impaction, all of the spines may be bowed, as above. In order to facilitate bowing all of the spines with this embodiment, a ring may be provided which allows pressure to be evenly applied to all of the flexible spines 14 at once. Once the selected spines 14 are bowed, the sheath 24 is extended over them and the remaining steps are taken as described above.

In another embodiment, the apparatus includes a shaft 12 which has a proximal end, a distal end, and a longitudinal axis. The shaft 12 is inserted through a fecal impaction. The apparatus includes at least two flexible spines 14. The first flexible spine 14 is coupled proximally or distally to said shaft 12, and is fixed in position. The first spine 14 may be coupled directly to the shaft 12, or it may be coupled to collars which are coupled to the shaft 12. The spine 14 should be fixed at only one end, so that the spine 14 may be bowed by any of the mechanisms described above.

The second flexible spine 14 is coupled to the shaft 12 in the same manner as the first flexible spine 14, except that it is rotatable about the longitudinal axis of the shaft 12. In one embodiment, a channel is provided which encircles the distal end of the shaft 12 and provides a groove in which the spine 14 may be moved. The spine 14 may be coupled to a rod which protrudes from the proximal end of the shaft 12. Rotation of the rod causes the second spine 14 to rotate.

Coupled to both spines 14 along their entire length is a sheath 24 of stiff material, as described above. In this embodiment, the sheath 24 is not extended to cover the spines 14 from end to end, as above. Instead, rotation of the second spine 14 about the longitudinal axis of the shaft 12 simultaneously cuts through the fecal impaction and deploys the sheath 24 in order to encapsulate the impaction. As above, once the fecal impaction is encapsulated by the sheath, the spines are straightened, and the apparatus is removed from the patient's rectum.

Although certain embodiments are specifically illustrated and described herein, it will be appreciated that many other modifications and variations of the present invention are possible in light of the above teachings, and within the purview of the appended claims, without departing from the spirit and intended scope of the invention. Other objects, features and advantages of the invention shall become apparent when the following drawings and claims are considered.

What is claimed is:

1. Apparatus for removing a fecal impaction from a patient's rectum, the apparatus comprising:

a shaft having proximal and distal ends;

a plurality of flexible spines arranged parallel to said shaft, each spine having proximal and distal ends, one of said proximal and distal ends of each spine fixed relative to a corresponding proximal or distal end of said shaft, each of said plurality of flexible spines comprising material providing said spines with sufficient thinness and stiffness to cut through a fecal impaction; and means for bowing at least one of said spines away from said shaft coupled to the other end of each spine such that said other end of each spine is slideable in a lengthwise mariner relative to said shaft and said bowed spine and said shaft define a volume which contains at least a portion of the fecal impaction.

2. The apparatus of claim 1 further comprising a collar fixed to one of said proximal and distal ends of said shaft, wherein said one end of each of said flexible spines is coupled to said fixed collar.

3. The apparatus of claim 1 wherein said means for bowing at least one of said flexible spines comprises a collar slideably mounted to one of said distal and proximal ends of said shaft, wherein a corresponding end of each of said flexible spines is coupled to said slideable collar.

4. The apparatus of claim 1 wherein said means for bowing at least one of said plurality of flexible spines comprises a plurality of rods, each of said plurality of rods extendible radially from said shaft and coupled to said spines.

5. The apparatus of claim 4 wherein said rods are located at said other end of said shaft and wherein said other end of said spines are coupled to said rods.

6. The apparatus of claim 4 wherein said rods are located at substantially the middle of said shaft and wherein said spines are coupled to said rods.

7. The apparatus of claim 1 further comprising:

a sheath having a fixed edge coupled to said proximal end of at least one of said plurality of flexible spines and a moveable edge slideably coupled to at least one of said plurality of flexible spines; and means for extending said sheath to cover at least one of said plurality of flexible spines from proximal end to distal end, thereby encapsulating the volume defined by said shaft and said flexible spine.

8. The apparatus of claim 7 wherein said sheath-extending means is a wire coupled to said moveable edge of said sheath.

9. The apparatus of claim 7 wherein said sheath includes a plurality of rings, said plurality of rings slideably attached to said plurality of flexible spines.

10. The apparatus of claim 1 wherein said distal end of said shaft is substantially conical in shape.

11. Apparatus for removing a fecal impaction from a patient's rectum, the apparatus comprising:

a shaft having proximal and distal ends;

a collar fixed to said proximal end of said shaft, said collar defining a plurality of orifices; and a plurality of flexible spines arranged parallel to said shaft, each spine having a distal end fixed relative to said distal end of said shaft and a proximal end extending a predetermined length through one of said orifices defined by said collar.

12. The apparatus of claim 11 further comprising a collar fixed to said distal end of said shaft, wherein said distal end of each of said spines is coupled to said distally-fixed collar.

13. The apparatus of claim 12 further comprising a plurality of rods, each of said plurality of rods extendible radially from said shaft and coupled to said spines.

14. The apparatus of claim 11 further comprising:

a sheath having a fixed edge coupled to said proximal end of at least one of said plurality of flexible spines and a moveable edge slideably coupled to at least one of said plurality of flexible spines; and means for extending said sheath to cover at least one of said plurality of flexible spines from proximal end to distal end, thereby encapsulating the volume defined by said shaft and said flexible spine.

15. The apparatus of claim 14 wherein said sheath-extending means is a wire coupled to said moveable edge of said sheath.

16. The apparatus of claim 14 wherein said sheath includes a plurality of rings, said plurality of rings slideably attached to said plurality of flexible spines.

17. The apparatus of claim 11 wherein said distal end of said shaft is substantially conical in shape.

18. A method for removing a fecal impaction from a patient's rectum comprising the steps of:

inserting an apparatus into the patient's rectum, said apparatus comprising a shaft having proximal and distal ends, a plurality of flexible spines fixed relative to one of said proximal and distal ends of said shaft, and a sheath disposed over said flexible rods;

bowing at least one of said flexible spines away from said shaft;

extending said sheath along the length of said bowed spines to encapsulate at least a portion of the fecal impaction;

straightening said bowed spines to compress the encapsulated fecal impaction; and removing said apparatus and the encapsulated fecal impaction from the patient's rectum.

19. The method of claim 18 wherein step (b) comprises bowing said plurality of flexible spines away from said shaft.

20. The method of claim 18 wherein step (b) further comprises cutting through the fecal impaction with said at least one bowed flexible spine.

21. The method of claim 18 wherein step (a) further comprises providing an apparatus in which the sheath has an inside surface and an outside surface, wherein a lubricant is disposed on said outside surface.

22. The method of claim 18 wherein step (a) further comprises inserting an apparatus into the patient's rectum, said apparatus comprising a shaft having proximal and distal ends, a collar slideably mounted on one of said proximal and distal ends of said shaft, a plurality of flexible spines, one end of said spines coupled to said collar and the other end of said spines fixed relative to said one end of said shaft, and a sheath disposed over said flexible spines, and wherein step (b) comprises sliding said collar toward the other of said proximal and distal ends of said shaft.

23. The method of claim 18 wherein step (a) further comprises inserting said apparatus to one side of the fecal impaction.

24. The method of claim 18 wherein step (a) further comprises inserting said apparatus through the fecal impaction.

25. Apparatus for removing a fecal impaction from a patient's rectum, the apparatus comprising:

a shaft having a proximal end, a distal end, and a longitudinal axis;

a first flexible spine fixed relative to said proximal and distal ends of said shaft, said first flexible spine fixed in position;

a second flexible spine fixed relative to said proximal and distal ends of said shaft, said second flexible spine rotatable about said longitudinal axis of said shaft;

a sheath having a first side coupled to said fixed spine and a second edge coupled to said rotatable spine; and means for bowing said flexible spines away from said shaft.

26. A method for treating a fecal impaction comprising the steps of:

(a) inserting the apparatus of claim 25 through the fecal impaction;

(b) bowing said flexible spines away from said shaft;

(c) rotating said rotatable spine around said shaft to encapsulate the fecal impaction with said sheath;

(d) straightening said bowed spines; and (e) removing said apparatus from the patient's rectum.

27. A device for removing a fecal impaction from a patient's rectum comprising:

a shaft having distal and proximal ends, said shaft defining a wire channel, said distal end of said shaft defining a wire orifice, and said proximal end of said shaft defining a handle orifice;

a collar slideably mounted on said distal end of said shaft;

a plurality of flexible spines, each of said spines having a distal end attached to said slideable collar and a proximal end attached to said proximal end of said shaft;

a sheath having a fixed edge coupled to said proximal ends of said spines and a moveable edge slideably mounted on said plurality of flexible spines; and a wire radially coupled to said sheath, wherein said wire passes through said wire orifice, is disposed in said wire channel, and exits said handle orifice.

28. The device of claim 27 wherein said sheath is folded accordion-like before it is extended.

29. The device of claim 27 wherein said moveable edge comprises an elastic ring, wherein said elastic ring is stiff enough to cut through the fecal impaction.

30. Apparatus for removing a fecal impaction from a patient's rectum, the apparatus comprising:

a shaft having proximal and distal ends;

a plurality of flexible spines arranged parallel to said shaft, each spine having proximal and distal ends, said proximal end of each spine fixed relative to said proximal end of said shaft and said distal end of each spine fixed relative to said distal end of said shaft;

means for shortening said shaft so that said spines bow away from said shaft such that said bowed spines and said shaft define a volume which contains at least a portion of the fecal impaction;

a sheath having a fixed edge coupled to said proximal end of at least one of said plurality of flexible spines and a moveable edge slideably coupled to at least one of said plurality of flexible spines; and means for extending said sheath to cover at least one of said plurality of flexible spines from proximal end to distal end, thereby encapsulating the volume defined by said shaft and said flexible spine.

31. The apparatus of claim 30 wherein said sheath-extending means is a wire coupled to said moveable edge of said sheath.

32. The apparatus of claim 30 wherein said sheath includes a plurality of rings, said plurality of rings slideably attached to said plurality of flexible spines.

* * * * *